United States Patent

Castro et al.

[11] Patent Number: 6,080,875
[45] Date of Patent: Jun. 27, 2000

[54] METHOD FOR PREPARING 2-THIENYLETHYLAMINE DERIVATIVES

[75] Inventors: Bertrand Castro, Saint Aunes; Jean-Robert Dormoy, Sisteron, both of France; Aldo Previero, Masi, Italy

[73] Assignee: Sanofi-Synthelabo, Paris, France

[21] Appl. No.: 09/380,450

[22] PCT Filed: Mar. 5, 1998

[86] PCT No.: PCT/FR98/00441

§ 371 Date: Sep. 2, 1999

§ 102(e) Date: Sep. 2, 1999

[87] PCT Pub. No.: WO98/39322

PCT Pub. Date: Sep. 11, 1998

[30] Foreign Application Priority Data

Mar. 5, 1997 [FR] France ................ 97/02621

[51] Int. Cl.$^7$ ............................... C07D 333/22
[52] U.S. Cl. ................................. 549/77
[58] Field of Search ................................. 549/77

[56] References Cited

U.S. PATENT DOCUMENTS 4,873,343 10/1989 Radisson .
5,132,435 7/1992 Bousquet et al. .
5,204,469 4/1993 Descamps et al. .

FOREIGN PATENT DOCUMENTS 321349 6/1989 European Pat. Off. .
355170 2/1990 European Pat. Off. .
465358 1/1992 European Pat. Off. .
466569 1/1992 European Pat. Off. .

OTHER PUBLICATIONS

Dullaghan et al., Journal Organic Chemistry, vol. 17, 1183–1186 (1952).
Browne et al., Journal Organic Chemistry, vol. 17, 1187–1193 (1952).

*Primary Examiner*—Deborah C. Lambkin
*Attorney, Agent, or Firm*—Michael D. Alexander

[57] ABSTRACT

The present invention relates to a process for the preparation of 2-thienylethylamine derivatives of general formula:

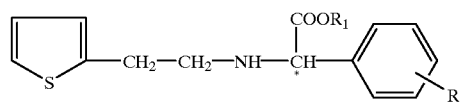

I as well as their acid addition salts, in which R represents a halogen atom and $R_1$ represents a $C_1$–$C_4$ alkyl group, characterized in that a thienylglycidic derivative of general formula:

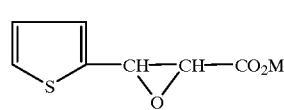

II in which M represents an alkali metal atom or a fraction of an alkaline-earth metal atom, is reacted with a phenylglycine ester, optionally in the form of a strong acid salt, of general formula:

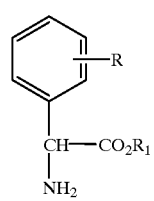

III in which R and $R_1$ have the same meaning as above, in the presence of an alkali metal borchydride of general formula:

$$X-Y \qquad \text{IV}$$

in which X represents an alkali metal atom and Y represents a group of formula:

$$-BH_3CN \text{ or } -BH_{(4-w)}Z_w$$

in which Z represents a carboxylic acid residue and optionally in the presence of a $C_1$–$C_4$ carboxylic acid, which gives the desired compound in the form of a free base which can be treated, if necessary, with an acid in order to obtain an addition salt of this compound.

20 Claims, No Drawings

METHOD FOR PREPARING 2-THIENYLETHYLAMINE DERIVATIVES

This application ia a 371 of PCT/FR98/00441 Mar. 5, 1998.

The present invention relates, in a general way, to a new process for the preparation of 2-thienylethylamine derivatives.

In particular, the invention relates to a new process for the preparation of N-phenylacetic derivatives of 2-thienylethylamine of general formula:

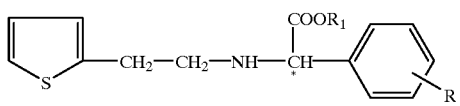

I as well as of their acid addition salts, in which R represents a halogen atom such as chlorine or bromine and $R_1$ represents a $C_1$–$C_4$ alkyl group, preferably methyl.

These compounds of formula I possess an asymmetric carbon represented by the asterisk and, consequently, may exist in the form of a racemic mixture or of individual optical isomers (−)-R and (+)-(S).

Thus, the invention relates to the preparation of 2-thienylethylamine derivatives of formula I, whether they are in the form of a racemic mixture or of individual dextrorotatory or laevorotatory enantiomers.

In formula I above, the R group may be present at the ortho, meta or para position with respect to the acetate group, preferably at the ortho position.

Moreover, chlorine represents a preferred R group.

Consequently and according to a preferred aspect, the invention relates to a process for the preparation of the (+)-(S) enantiomer of the compounds of formula I, in particular the (+)-(S) enantiomer of methyl α-(2-thienyl-2-ethylamino)-α-(2-chlorophenyl)acetate.

These compounds of formula I are known products and may be used for the preparation of pharmacologically active compounds.

For example, methyl (+)-(S)-α-(2-thienyl-2-ethylamino)-α-(2-chlorophenyl)acetate has been described in patent EP 466569 as well as its use for the preparation of methyl (+)-(S)-α-(4,5,6,7-tetrahydrothieno[3,2-c]-5-pyridyl)-α-(2-chlorophenyl)acetate or clopidogrel.

This enantiomer having the structural Formula:

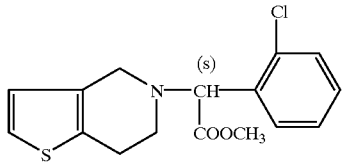

is known for its value in therapy in particular for its anti-platelet aggregation and antithrombotic activities.

A process for the preparation of clopidogrel via a racemic compound, namely methyl (R,S)-α-(4,5,6,7-tetrahydrothieno[3,2-c]-5-pyridyl)-α-(2-chlorophenyl) acetate which is subjected to a resolution process, has been described in this patent EP 466569.

According to this process, a diastereoisomeric salt of this racemic compound is selectively crystallized with (−)-(R)-10-camphorsulphonic acid, which leads to the chiral camphorsulphonate of clopidogrel and the base is then released therefrom by displacing the (−)-(R)-10-camphorsulphonic acid.

This route of access, although conventionally used to prepare a chiral compound, may be considered not to be very convenient from the economic point of view since it requires both the recycling of the unwanted isomer and that of the salt of the chiral (−)-(R)-10-camphorsulphonic acid used in the resolution.

A more convergent method for the preparation in particular of clopidogrel was proposed in patent EP 466569, a method according to which methyl (+)-2-chlorophenylglycinate is treated, in a first step, with a 2-thienylethyl halide or sulphonate, in a solvent, for several hours, at a temperature of between 50° C. and 100° C. and in the presence of a base, in order to give, after salification, methyl (+)-(S)-α-(2-thienyl-2-ethylamino)-α-(2-chlorophenyl)acetate hydrochloride with a yield of about 50%.

However, it has been observed that the choice of the solvent, in this method, is not unimportant if it is desired to obtain only one of the enantiomers of methyl α-(2-thienyl-2-ethylamino)-α-(2-chlorophenyl)acetate by reaction of one of the enantiomers of methyl 2-chlorophenylglycinate, partial racemization occurring in some solvents.

Moreover, this process has the disadvantage of requiring a fairly extended contact time at a temperature above ambient, for example for 40 hours at 80° C., for the production of methyl (+)-(S)-α-(2-thienyl-2-ethylamino)-α-(2-chlorophenyl)acetate, these operating conditions only being able to negatively influence the cost price of the final product.

Finally, the yields of 2-thienylethylamine derivatives of formula I thus obtained remain relatively modest since they are of the order of 50%.

The search for an industrial process for the preparation of 2-thienylethylamine derivatives of formula I, whether they are in racemic form or in the form of individual enantiomers, using synthesis intermediates according to an operating process which is inexpensive and which provides a satisfactory yield of desired product, remains of unquestionable interest.

However, it has now been found, surprisingly, that it is possible to obtain the 2-thienylethylamine derivatives of formula I, in particular their dextrorotatory enantiomers, while avoiding the disadvantages reported above and in yields greater than those obtained with the previous process since the formation of at least 90% of these compounds in the form of a free base relative to the theoretical yield is recorded.

Thus, according to the invention, 2-thienylethylamine derivatives of formula I are prepared by reacting a thienylglycidic derivative of general formula:

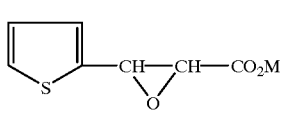

II in which M represents an alkali metal atom such as lithium, potassium or preferably sodium or a fraction of an alkaline-earth metal atom such as calcium ½ or magnesium ½ with a phenylglycine ester of general formula:

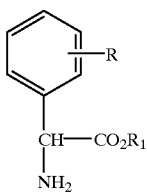

in which R and $R_1$ have the same meaning as above for I, optionally in the form of a strong acid salt, for example hydrochloride or methanesulphonate, in the presence of an alkali metal borohydride of general formula:

$$X—Y \qquad \text{IV}$$

in which X represents an alkali metal atom, preferably sodium, and Y represents a group of formula:

$$—BH_3CN \text{ or } —BH_{(4-w)}Z_w$$

in which Z represents a carboxylic acid residue, generally a residue of general formula:

$$R_2—CO_2—$$

in which $R_2$ represents a $C_1$–$C_{10}$ alkyl, for example methyl, and w represents 1, 2 or 3, which gives the desired compound in the form of a free base which can be reacted, if necessary, with an acid in order to obtain an addition salt of this compound.

The compound of formula III may be in racemic form or, on the contrary, in the form of (+)-(S) or (−)-(R) enantiomers.

In fact, it has been possible to demonstrate that the process of the invention is carried out with retention of configuration when the phenylglycine ester of formula III is in the form of a separate dextrorotatory or laevorotatory enantiomer, the optical purity of the enantiomer of the compound of formula I depending exclusively on the optical purity of the enantiomer of the starting compound of formula III.

Because of this stereospecificity of the process of the invention, the esters of formula III in the form of individual enantiomers, in particular methyl (+)-(S)-α-amino-α-(2-chlorophenyl)acetate, may be considered as being preferred.

When the alkali metal borohydride corresponds to a cyanoborohydride, that is to say a compound of formula IV in which Y represents the —BH$_3$CN group, the process of the invention is advantageously and preferably carried out in the presence of a weak acid such as a $C_1$–$C_4$ alkylcarboxylic acid, for example acetic acid, and preferably at a concentration not exceeding 0.50 mol/l.

As a guide, a maximum yield of compound of formula I has been recorded at a concentration of 0.30 to 0.35 mol/l of weak acid such as acetic acid in the organic solvent used, for example methanol.

Likewise, when the compound of formula IV is an alkali metal cyanoborohydride, there are used:

a) a strong acid salt of the compound of formula III, in particular of a compound of formula III in which R represents a halogen atom at the ortho position, in general a strong acid salt of a 2-chlorophenyl derivative of formula III and more particularly a strong acid salt of methyl α-amino-α-(2-chlorophenyl)acetate, b) the thienyl derivative of formula II, preferably in a slight excess relative to the compound of formula III, up to 0.5 mol in excess per mol of compound of formula III.

Likewise, when the alkali metal borohydride corresponds to an acyloxyborohydride, that is to say a compound of formula IV in which Y represents the —BH$_{(4-w)}$Z$_w$ group, the process of the invention is preferably carried out in a weak acid as solvent such as a $C_1$–$C_4$ alkylcarboxylic acid, for example acetic acid in the absence of another solvent.

However, it is also possible to use a reaction medium consisting of an organic solvent such as of the alcohol type, for example methanol or a hydrocarbon, halogenated or otherwise, such as benzene, toluene or xylene or alternatively dichloromethane, and of a weak acid as above. In this case, the weak acid in question is preferably present in an amount of at least 50% by volume relative to the organic solvent.

Moreover, when the compound of formula IV is an alkali metal acyloxyborohydride, equimolar quantities of this compound of formula IV and of phenylglycine ester of formula III are generally used, this compound of formula III being preferably used in excess, that is to say up to 2.2 molar equivalents per molar equivalent of thienylglycidic derivative of formula II.

As for the alkali metal borohydrides of formula IV, they comprise in particular alkali metal cyanoborohydrides, preferably sodium cyanoborohydride (NaBH$_3$CN) but also borohydrides of carboxylic acid residues. These may be obtained immediately before use in an appropriate solvent such as dichloromethane by mixing a borohydride of general formula:

$$XBH_4 \qquad \text{VI}$$

in which X has the same meaning as above, for example sodium, with a carboxylic acid of general formula:

$$R_2—CO_2H \qquad \text{VII}$$

in which $R_2$ has the same meaning as above.

According to customary use, the borohydrides of formula IV in which Y represents a -BH$_{(4-w)}$Z$_w$ group are prepared either a) by slow addition, with stirring, of an alkali metal borohydride of formula XBH$_4$ in which X has the same meaning as above, for example sodium borohydride, to an acid of formula VII, which may be in stoichiometric excess, for example acetic acid, this acid being cooled to a temperature less than room temperature, or b) by slow addition, with stirring, of 1 to 3 molar equivalents of acid of formula VII to a suspension of alkali metal borohydride of formula XBH$_4$ as above and in the chosen organic solvent, for example dichloromethane.

After removal of the solvent, the residue taken up in an acid of formula VII may constitute an appropriate reaction medium For carrying out the process of the invention.

The borohydrides of formula IV used in the process of the invention are generally used at a concentration which does not exceed 0.40 mol/l, the latter substantially corresponding to the saturating concentration, that is to say the concentration above which the yield of the reaction no longer increases.

The thienylglycidic derivatives of formula II may be prepared according to known methods.

For example, they may be obtained by application of the process proposed in patent EP 465358 based on a Darzens reaction.

According to this method, 2-thienylcarboxaldehyde is reacted, in isopropanol and at room temperature, with isopropyl haloacetate, for example isopropyl chloroacetate in the presence of an alkali metal isopropoxide, preferably sodium isopropoxide, which provides isopropyl 2-thienylglycidate which is then saponified by means of an alkali metal or alkaline-earth metal hydroxide, to finally obtain the desired glycidate or glycidic ester of formula II.

More generally, this method may be used starting with a methyl haloacetate such as methyl chloroacetate, the reaction being carried out in a $C_1$–$C_4$ alkanol, for example methanol.

As for the glycine esters of formula III, they are also known compounds which may be prepared by known methods, whether they are in (−)-(R), (+)-(S) form or in racemic form.

To this effect, it is possible to use the method described in patent EP 466569 according to which the corresponding racemic amino acid or its individual enantiomers is esterified by reacting with thionyl chloride and a $C_1$–$C_4$ alkanol.

Likewise, the strong acid salts of the enantiomers of the esters of formula III may also be obtained by recrystallization of the salt formed by the racemate of the same compound of formula III with an optically active acid such as (+) or (−)-tartaric acid in isopropanol or alternatively the (+) or (−)-10-camphorsulphonic acids in acetone in the presence or not of methyl ethyl ketone, and then by treating with an appropriate strong acid in order to obtain the desired salt.

Alternatively, it is possible to prepare the individual enantiomers of the esters of formula III in the form of a strong acid salt starting with the enantiomer, having the opposite configuration, of the said ester, optionally in the form of a mixture with the desired enantiomer of the said ester, this starting ester being in the form of a base or of a weak acid addition salt, for example in acetate form.

According to this process, the starting enantiomer or mixture of enantiomers optionally in the presence of a polar or apolar cosolvent such as isopropanol, or a mixture of such cosolverts, is treated with a ketone compound, preferably acetone and with an N-protected α-amino acid, namely N-(2,4-dinitrobenzoyl)phenylglycine in the form of an enantiomer, the treatment taking place in the presence of a carboxylic acid, preferably acetic acid, so as to induce total racemization and the concomitant precipitation of a diastereoisomeric salt of the ester of formula III and of the N-(2,4-dinitrobenzoyl)phenylglycine. The diastereoisomeric salt in question is subsequently hydrolysed, in the presence of a strong acid such as hydrochloric acid, in order to obtain the desired enantiomer of formula III in the form of a strong acid salt.

The following nonlimiting examples illustrate the process of the invention.

PREPARATIONS a) Sodium 2-thienylqlycidate 100 ml of methylene chloride, 8.3 ml of 2-thienylcarboxaldehyde at 98% and 9.3 ml of methyl chloroacetate are introduced into a 250-ml flask and the mixture is then homogenized by mechanical stirring.

The mixture is placed on a bath at 0° C. (ice/water) and then 18 ml of sodium methoxide at 30% are slowly added over one hour. The addition is continued for 2 hours while still cold and the temperature is then allowed to return to room temperature. 50 g of ice cubes are then added to the reaction medium and the mixture is stirred until complete dissolution is obtained. The medium is transferred to a separating funnel and the two phases are separated. The organic phase is washed with 50 ml of 0.5 N hydrochloric acid and then once with distilled water. It is dried over anhydrous sodium sulphate and filtered. It is concentrated under vacuum at a temperature of less than 30° C. and then it is allowed to return to 0° C. on an ice bath. 50 ml of absolute ethanol and 16 ml of sodium methoxide at 30% are then poured over the oily residue and then 1.6 ml of distilled water are slowly added, which causes the immediate formation of a precipitate. This precipitate is placed in a cold room for 12 hours and then it is drained, it is washed with absolute ethanol and then with ethyl ether. It is then dried in a desiccator.

14.6 g of sodium 2-thienylglycidate are obtained in this manner.

b) (R,S)-α-Amino-α-(2-chlorophenyl)acetic acid 6.88 g of ammonium chloride, 11.64 g of potassium cyanide and 200 ml of aqueous ammonia at 30% are introduced into a 500-ml flask. 200 ml of methanol containing 11.2 ml of 2-chlorobenzaldehyde at 99% are then added, with mechanical stirring, and then the reaction medium is heated at 45° C. for one hour, with occasional stirring. The mixture is then diluted with 200 ml of distilled water and extracted twice with 200 ml of ethyl acetate.

The organic phases are combined and then they are washed with distilled water. The medium is dried over anhydrous sodium sulphate, filtered and evaporated to dryness, which gives an oily residue.

This residue is then hydrolysed by addition of 200 ml of 6 N hydrochloric acid, the medium is heated to reflux temperature and left for a minimum of 4 hours. The hydrolysate is washed with chloroform until the yellow colour due to the excess of reagent disappears and then the excess of hydrochloric acid is evaporated by reducing the volume by half by evaporation under vacuum. 100 ml of hot distilled water are added and the pH is adjusted to 5.27 with aqueous ammonia, which causes an onset of precipitation of (R,S)-α-amino-α-(2-chlorophenyl)acetic acid.

The medium is then left in a cold room for 12 hours, drained and dried under vacuum in the presence of phosphoric anhydride, so as to obtain 8.45 g of (R,S)-α-amino-α-(2-chlorophenyl)acetic acid in the form of white crystals.

c) Methyl (R,S)-α-amino-α-(2-chlorophenyl)acetate hydrochloride 5 ml of thionyl chloride are slowly added, with magnetic stirring and on an ice bath, to 100 ml of methanol. The (R,S)-α-amino-α-(2-chlorophenyl)acetic acid crystals obtained above are then dissolved in this mixture and the reaction medium is heated to 40° C. The reaction is allowed to continue for 48 hours at 40° C. and then the medium is evaporated to dryness under vacuum. The residue is dissolved in methanol and the medium again evaporated under reduced pressure. 200 to 300 ml of ethyl ether are then added and the medium is left for 15 hours at 5 to 60° C., which causes the formation of crystals. These crystals are drained, they are washed with ethyl ether and they are dried under vacuum.

In this manner, 9.5 g of methyl (R,S)-α-amino-α-(2-chlorophenyl)acetate hydrochloride are obtained.

d) Methyl (+)-(S)-α-amino-α-(2-chlorophenyl)acetate (−)-(2,4-dinitrobenzoyl)phenylglycinate A suspension of 7.1 g of methyl (R,S)-α-amino-α-(2-chlorophenyl)acetate hydrochloride is prepared in 50 ml of ethyl acetate, and 50 ml of 2 to 3 molar aqueous ammonia are added thereto and extracted. The organic phase is separated and it is dried over anhydrous sodium sulphate.

The medium is filtered directly into a 500-ml container and then evaporated to dryness at a temperature of less than 40° C.

45 ml of isopropanol and 10 g of (−)-(2,4-dinitrobenzoyl) phenylglycine previously solubilized in 60 ml of acetone containing 5% of acetic acid are then added with magnetic stirring. The medium is then seeded with a few crystals of the desired compound, 120 ml of hexane are added and the stirring is maintained for 15 minutes. The medium is left for 18 hours at 35° C. and then for 24 hours at 5 to 6° C., which causes the formation of crystals which are drained, rinsed with an acetone/hexane vol./vol. mixture and dried.

In this manner, 9.5 g of methyl (+)-(S)-α-amino-α-(2-chlorophenyl)acetate (−)-(2,4-dinitrobenzoyl) phenylglycinate are obtained.

Optical purity: 98% (gas chromatography)

e) Methyl (+)-(S)-α-amino-α-(2-chlorophenyl)acetate hydrochloride 3 g of methyl (+)-(S)-α-amino-α-(2-chlorophenyl)acetate (−)-(2,4-dinitrobenzoyl)phenylglycinate are introduced into 20 ml of a 1 M solution of sodium carbonate and the mixture is extracted twice with 10 ml of ethyl acetate.

The combined organic phases are dried over anhydrous sodium sulphate and treated with 10 ml of 1 N hydrochloric acid in methanol and concentrated under vacuum. The residue is dissolved in the minimum quantity of methanol and the crystallization is triggered by addition of diethyl ether.

Methyl (+)-(S)-α-amino-α-(2-chlorophenyl)acetate hydrochloride is recovered in this manner with a practically quantitative yield.

f) Methyl (+)-(S)-α-amino-α-(2-chlorophenyl)acetate 2.36 g ($10^{-2}$ mol) of methyl (+)-(S)-α-amino-α-(2-chlorophenyl)acetate hydrochloride are introduced into 50 ml of ethyl acetate or of methylene chloride, and 20 ml of 1.5 M aqueous ammonia or of sodium bicarbonate at 5% are added. The medium is stirred, the organic phase is separated after settling out and the aqueous phase is extracted with 10 ml of ethyl acetate. The organic phases are pooled, treated with anhydrous sodium sulphate and concentrated under reduced pressure until distillate is absent. The residue consisting of methyl (+)-(S)-α-amino-α-(2-chlorophenyl)acetate is then taken up in 50 ml of acetic acid.

EXAMPLE 1

Methyl (+)-(S)-α-(2-thienyl-2-ethylamino)-α-(2-chlorophenyl)acetate hydrochloride 1.92 g ($10^{-2}$ mol) of sodium 2-thienylglycidate, 2.36 g of methyl (+)-(S)-α-amino-α-(2-chlorophenyl)acetate hydrochloride and 0.63 g ($10^{-2}$ mol) of sodium cyanoborohydride (NaBH3CN) as well as 40 ml of methanol and 0.8 ml of acetic acid are placed in a 100-ml flask.

This reaction medium is then maintained under magnetic stirring on a bath at 18° C. During the reaction, aliquot portions (10 µl) of the mixture are collected and they are analysed by high-performance liquid chromatography (HPLC) in order to monitor the formation of the desired compound at the same time as the disappearance of the methyl (S)-(+)-α-amino-α-(2-chlorophenyl)acetate. After 3 to 4 hours, the reaction is stabilized and analysis shows a yield of 66% of methyl (+)-(S)-α-(2-thienyl-2-ethylamino)-α-(2-chlorophenyl)acetate.

0.96 to 1 g ($0.5 \times 10^{-2}$ mol) of sodium 2-thienylglycidate, 0.3 g ($0.5 \times 10^{-2}$ mol) of NaBH$_3$CN and 0.4 ml of acetic acid are then added. After 3 hours of reaction, analysis shows a yield of 98% of desired compound in free base form and the disappearance of the starting ester.

The reaction mixture is then diluted with 250 to 300 ml of 1 to 2 M aqueous ammonia and the medium is extracted twice with ethyl acetate. The organic phases are then pooled, dried over sodium sulphate and evaporated. The residue is taken up in 40 to 50 ml of methanol and treated with 15 to 20 ml (excess) of 1 M hydrochloric acid in methanol. After evaporation, the methyl (+)-(S)-α-(2-thienyl-2-ethylamino)-α-(2-chlorophenyl)acetate hydrochloride crystallizes upon addition of acetone.

Yield: 2.56 g, that is to say 75%

EXAMPLE 2

Methyl (+)-(S)-α-(2-thienyl-2-ethylamino)-α-(2-chlorophenyl)acetate hydrochloride A methanolic solution containing 0.25 molar sodium 2-thienylglycidate, 0.25 molar methyl (+)-(S)-α-amino-α-(2-chlorophenyl)acetate hydrochloride, 0.25 molar NaBH$_3$CN and X molar acetic acid is introduced into a 100-ml flask.

This reaction medium is then maintained under magnetic stirring on a bath at 18° C. During the reaction, aliquot portions (10 µl) of the mixture are collected and they are analysed by HPLC in order to monitor the formation of the desired compound at the same time as the disappearance of the methyl (+)-(S)-α-(2-thienyl-2-ethylamino)-α-(2-chlorophenyl)acetate. After 3 to 4 hours, the reaction stabilizes and analysis shows the following yields of methyl (+)-(S)-α-amino-α-(2-chlorophenyl)acetate calculated on the conversion of the starting ester.

| X (molar) | Yield (%) |
| --- | --- |
| 0 | 50 |
| 0.125 | 52.5 |
| 0.167 | 57.4 |
| 0.330 | 66 |
| 0.420 | 56 |

The reaction is then continued as described in Example 1 so as to obtain first methyl (+)-(S)-α-(2-thienyl-2-ethylamino)-α-(2-chlorophenyl)acetate in basic form in yields varying from 80 to 98% by HPLC, and then the hydrochloride of this compound in yields of 60 to 80% after isolation.

EXAMPLE 3

Methyl (+)-(S)-α-(2-thienyl-2-ethylamino)-α-(2-chlorophenyl)acetate

This compound was prepared according to the method described in Example 1 by replacing the 0.37 molar NaBH$_3$CN solution (0.9 g in 40 ml of methanol) with a methanolic solution having the molarity indicated above, so as to obtain, by HPLC, the following yields of non-isolated methyl (+)-(S)-α-(2-thienyl-2-ethylamino)-α-(2-chlorophenyl)acetate. Molarity of NaBH$_3$CN Yield (%)

| Molarity of NaBH$_3$CN | Yield (%) |
| --- | --- |
| 0.22 | 90 |
| 0.30 | 97 |

EXAMPLE 4

Methyl (+)-(S)-α-(2-thienyl-2-ethylamino)-α-(2-chlorophenyl)acetate hydrochloride 1 g of sodium borohydride is suspended in 100 ml of dichloromethane, under cooling (water bath of 14 to 15° C.) and with magnetic stirring. 4.5 ml of acetic acid are then slowly added over 5 to 10 minutes. As soon as the release of hydrogen is complete, the dichloromethane is completely evaporated at reduced pressure and the residue obtained is then dissolved in the acetic solution of methyl (+)-(S)-α- amino-α-(2-chlorophenyl)acetate obtained in Preparation f) above. Three fractions, namely 1.54 g, 1.54 g and 1.34 g of sodium 2-thienylglycidate are then added, with mechanical stirring, at 5-minute intervals at a temperature of 15 to 18° C., and then the reaction is allowed to continue for 20 minutes after the last addition.

The reaction mixture is then diluted with 200 ml of ethyl acetate and 400 ml of water and then 70 ml of aqueous ammonia at 30% are then slowly added. The medium is stirred, the organic phase separated after settling out (the pH of the aqueous phase should be basic) and the aqueous phase is again extracted with 100 ml of ethyl acetate. The organic phases are pooled, washed with water, dried over sodium sulphate and concentrated under vacuum at reduced pressure. The residue obtained is then dissolved in 20 ml of 1 M hydrochloric acid in methanol and the medium is again evaporated. The residue is taken up in 60 ml of acetone and kept at room temperature until crystals are formed. 100 ml of tert-butyl methyl ether are then added, the medium is allowed to crystallize for 10 to 12 hours in a cold room and then the crystals formed are drained.

2.42 g of methyl (+)-(S)-α-amino-α-(2-chlorophenyl) acetate hydrochloride are recovered in this manner.

Analytical yield: 95%

Weight yield: 70% (analysis of the crystallization mother liquors shows the presence of non-precipitated desired compound).

EXAMPLE 5

Methyl (+)-(S)-α-(2-thienyl-2-ethylamino)-α-(2-chlorophenyl)acetate hydrochloride 1 g of sodium borohydride is added, with stirring and cooling and over about 10 minutes, to the acetic solution of methyl (+)-(S)-α-amino-α-(2-chlorophenyl)acetate obtained in Preparation f) above. 4.42 g of sodium 2-thienylglycidate are then introduced in 3 fractions and at a temperature of 15 to 18° C. and then allowed to react for 20 minutes after the last addition.

The procedure is then carried out as described in Example 4 in order to obtain methyl (+)-(S)-α-(2-thienyl-2-ethylamino)-α-(2-chlorophenyl)acetate hydrochloride.

Analytical yield: 95%

Weight yield: 70% (analysis of the crystallization mother liquors shows the presence of non-precipitated desired compound).

What is claimed is:

1. Process for the preparation of 2-thienylethylamine derivatives of general formula:

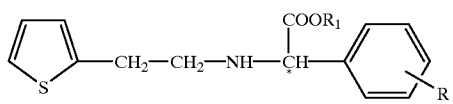

I as well as their acid addition salts, in which R represents a halogen atom and $R_1$ represents a $C_1$–$C_4$ alkyl group wherein a thienylglycidic derivative of general formula:

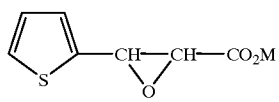

II in which M represents an alkali metal atom or a fraction of an alkaline-earth metal atom, is reacted with a phenylglycine ester, optionally in the form of a strong acid salt, of general formula:

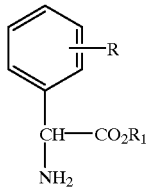

III in which R and $R_1$ have the same meaning as above, in the presence of an alkali metal borohydride of general formula:

X—Y    IV in which X represents an alkali metal atom and Y represents a group of formula:

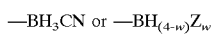

in which Z represents a carboxylic acid residue and w represents 1, 2 or 3, which gives the desired compound in the form of a free base which can be treated, if necessary, with an acid in order to obtain an addition salt of this compound.

2. Process according to claim 1 wherein the halogen atom is situated at the ortho position.

3. Process according to claim 1 wherein the halogen atom is chlorine.

4. Process according to claim 3 wherein $R_1$ represents methyl.

5. Process according to claim 4 wherein the 2-thienylethylamine derivative of formula I and the phenylglycine ester of formula III are each in (+)-(S) enantiomer form.

6. Process according to claim 1 wherein M represents lithium, sodium, potassium, calcium ½ or magnesium ½.

7. Process according to claim 1 wherein the phenylglycine ester of formula III is in the form of a strong acid salt chosen from hydrochloride or methanesulphonate.

8. Process according to claim 1 wherein Z represents a carboxylic acid residue of general formula:

in which $R_2$ represents a $C_1$–$C_{10}$ alkyl group.

9. Process according to claim 1 wherein the alkali metal borohydride corresponds to sodium cyanoborohydride.

10. Process according to claim 9 wherein the reaction is carried out in the presence of a $C_1$–$C_4$ alkylcarboxylic acid.

11. Process according to claim 10 wherein the carboxylic acid is used at a concentration not exceeding 0.50 mol/l.

12. Process according to claim 11 wherein the carboxylic acid is used at a concentration of 0.30 to 0.35 mol/l.

13. Process according to claim 9 wherein the carboxylic acid is acetic acid.

14. Process according to claim 9 wherein the phenylglycine ester of formula III is in the form of a strong acid salt.

15. Process according to claim 1 wherein the thienylglycidic derivative of formula II is used in excess, up to an additional 0.5 mol per mol of phenylglycine ester of formula III.

16. Process according to claim 1 wherein the alkali metal borohydride coresponds to a compound of formula IV in which Y represents the $-BH_{(4-w)}Z_w$ group.

17. Process according to claim 16 wherein the reaction is carried out in a $C_1-C_4$ alkylcarboxylic acid.

18. Process according to claim 16 wherein the phenylglycine ester of formula III is used in excess up to 2.2 molar equivalents per molar equivalent of thienylglycidic derivative of formula II.

19. Process according to claim 1 wherein the alkali metal borohydride of formula IV is used at a concentration not exceeding 0.40 mol/l.

20. Process according to claim 5 wherein methyl (+)-(S)-α-(2-thienyl-2-ethylamino)-α-(2-chlorophenyl)acetate is prepared.

* * * * *